United States Patent
Su et al.

(10) Patent No.: US 6,844,208 B2
(45) Date of Patent: Jan. 18, 2005

(54) METHOD AND SYSTEM FOR MONITORING IMPLANTATION OF IONS INTO SEMICONDUCTOR SUBSTRATES

(75) Inventors: Jin Ming Su, Shanghai (CN); Xiao Sheng Qiang, Shanghai (CN); Li Zi Wang, Shanghai (CN); Chin Te Hunag, Shanghai (CN)

(73) Assignee: Semiconductor Manufacturing International (Shanghai) Corporation, Shanghai (CN)

(*) Notice: Subject to any disclaimer, the term of this patent is extended or adjusted under 35 U.S.C. 154(b) by 0 days.

(21) Appl. No.: 10/462,028

(22) Filed: Jun. 12, 2003

(65) Prior Publication Data

US 2004/0253752 A1 Dec. 16, 2004

(51) Int. Cl.[7] .......................... H01L 21/66; G01R 31/26
(52) U.S. Cl. ............................. 438/17; 438/14; 438/18
(58) Field of Search ............................ 438/14, 17, 18, 438/514, 530

(56) References Cited

U.S. PATENT DOCUMENTS 6,754,553 B2 * 6/2004 Wieczorek et al. ......... 700/121

* cited by examiner

*Primary Examiner*—Michael S. Lebentritt
*Assistant Examiner*—Beth E. Owens
(74) *Attorney, Agent, or Firm*—Townsend and Townsend and Crew, LLP

(57) ABSTRACT

A method for monitoring a dose of a silicon bearing implant is described. The method includes introducing a first implant species through a surface of a semiconductor substrate at a first does of energy level and introducing a silicon bearing species through the surface of the semiconductor substrate at a second dose and a second energy level. The method anneals the semiconductor substrate and measures a sheet resistance value of the surface of the semiconductor substrate. The method also determines the second dose value based upon the surface resistance value.

20 Claims, 3 Drawing Sheets

METHOD AND SYSTEM FOR MONITORING IMPLANTATION OF IONS INTO SEMICONDUCTOR SUBSTRATES

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention is directed to integrated circuits and their processing for the manufacture of semiconductor devices. More particularly, the invention provides a method and system for monitoring implantation of silicon bearing species in semiconductor substrates for integrated circuit device structures. But it would be recognized that the invention has a much broader range of applicability. For example, the invention can be applied to a variety of devices such as dynamic random access memory devices (DRAM), static random access memory devices (SRAM), application specific integrated circuit devices (ASIC), microprocessors and microcontrollers, flash memory devices, and others.

Integrated circuits or "ICs" have evolved from a handful of interconnected devices fabricated on a single chip of silicon to millions of devices. Current ICs provide performance and complexity far beyond what was originally imagined. In order to achieve improvements in complexity and circuit density (i.e., the number of devices capable of being packed onto a given chip area), the size of the smallest device feature, also known as the device "geometry", has become smaller with each generation of ICs. Semiconductor devices are now being fabricated with features less than a quarter of a micron across.

Increasing circuit density has not only improved the complexity and performance of ICs but has also provided lower cost parts to the consumer. An IC fabrication facility can cost hundreds of millions, or even billions, of dollars. Each fabrication facility will have a certain throughput of wafers, and each wafer will have a certain number of ICs on it. Therefore, by making the individual devices of an IC smaller, more devices may be fabricated on each wafer, thus increasing the output of the fabrication facility. Making devices smaller is very challenging, as each process used in IC fabrication has a limit. That is to say, a given process typically only works down to a certain feature size, and then either the process or the device layout needs to be changed.

As merely an example, implantation is a process that often needs to be changed with feature size. Implantation is often used to introduce impurities to change an electrical characteristic of the semiconductor substrate from a first type to second type. Here, P-type impurities and N-type impurities are often introduced into the substrate during one or more steps in the process of manufacturing integrated circuits. Such impurities are often characterized by dose and energy level, as well as other parameters, to control and maintain the manufacturing process. Implantation dose is often measured using a tool from Thermal Wave, such as the TP 500, but can also be others. Silicon bearing impurities have also been used with the implantation process. Such silicon bearing impurities are often used in salicide Si implant and Si pre-amorphous. Unfortunately, many limitations exist in monitoring the dose of the silicon bearing impurities. That is, small changes in implantation doses often cannot be detected using conventional measurement tools. Accordingly, it becomes difficult to maintain monitor dosage levels of silicon bearing impurities in conventional processing such as implantation tools.

From the above, it is seen that an improved technique for processing semiconductor devices is desired.

BRIEF SUMMARY OF THE INVENTION

According to the present invention, techniques including methods for the manufacture of semiconductor devices are provided. More particularly, the invention provides a method and system for monitoring implantation of silicon bearing species in semiconductor substrates for integrated circuit device structures. But it would be recognized that the invention has a much broader range of applicability. For example, the invention can be applied to a variety of devices such as dynamic random access memory devices (DRAM), static random access memory devices (SRAM), application specific integrated circuit devices (ASIC), microprocessors and microcontrollers, flash memory devices, and others.

In a specific embodiment, the invention provides a method for monitoring a dose of a silicon bearing implant. The method includes introducing a first implant species through a surface of a semiconductor substrate at a first dose and a first energy level and introducing a silicon bearing species through the surface of the semiconductor substrate at a second dose and a second energy level. The method anneals the semiconductor substrate and measures a sheet resistance value of the surface of the semiconductor substrate. The method also determines the second dose value based upon the surface resistance value. In an alternative specific embodiment, the invention provides a method for manufacturing integrated circuits on semiconductor substrates. The method includes inserting a test substrate into an implant tool. The method also includes introducing a base implant species through a surface of the test substrate at a base dose and a base energy level and introducing a silicon bearing species through the surface of the test substrate at a first dose and a first energy level. The method anneals the test substrate in an inert environment to activate the base implant species in the test substrate. The method measures a sheet resistance value of the surface of the test substrate. A step of determining the first dose value based upon at least the surface resistance value is included. The method uses the first dose to calibrate the implantation tool for a manufacture of semiconductor substrates and uses the implantation tool for the manufacture of semiconductor substrates.

Many benefits are achieved by way of the present invention over conventional techniques. For example, the present technique provides an easy to use process that relies upon conventional technology. In some embodiments, the method provides higher device yields in dies per wafer. Additionally, the method provides a process that is compatible with conventional process technology without substantial modifications to conventional equipment and processes. Preferably, the invention can be applied to a variety of applications such as memory, ASIC, microprocessor, and other devices. Depending upon the embodiment, one or more of these benefits may be achieved. These and other benefits will be described in more throughout the present specification and more particularly below.

Various additional objects, features and advantages of the present invention can be more fully appreciated with reference to the detailed description and accompanying drawings that follow.

DETAILED DESCRIPTION OF THE INVENTION

According to the present invention, techniques including methods for the manufacture of semiconductor devices are provided. More particularly, the invention provides a method for forming small features such as contacts for integrated circuit device structures. But it would be recognized that the invention has a much broader range of applicability. For example, the invention can be applied to a variety of devices such as dynamic random access memory devices (DRAM), static random access memory devices (SRAM), application specific integrated circuit devices (ASIC), microprocessors and microcontrollers, flash-memory devices, and others.

A method according to an embodiment of the present invention for identifying a concentration of silicon bearing impurities for implantation is provided as follows:

1. Provide test wafer;
2. Implant test wafer using arsenic bearing impurities at first dose and first energy;
3. Implant silicon bearing impurities at second dose and second energy into the test wafer;
4. Anneal implanted test wafer;
5. Measure sheet resistance of implanted test wafer;
6. Repeat steps 1 through 5 for other test wafers using different dosages;
7. Form correlation between dosages and sheet resistance values;
8. Use correlation between dosages and sheet resistance values for at least one other test wafer or other test wafers;
9. Adjust implant process for the other test wafer; and
10. Perform other steps, as desired.

The present invention provides the above method for using test wafers to adjust an implantation process for correlation or calibration purposes. Such test wafers are not often production wafers. Sheet resistance values are used to correlate or calibrate the implantation process. The present method allows a user of the implantation process to adjust the process for implanting silicon bearing impurities. Further details of the present invention can be found throughout the present specification and more particularly below.

Figure 1:
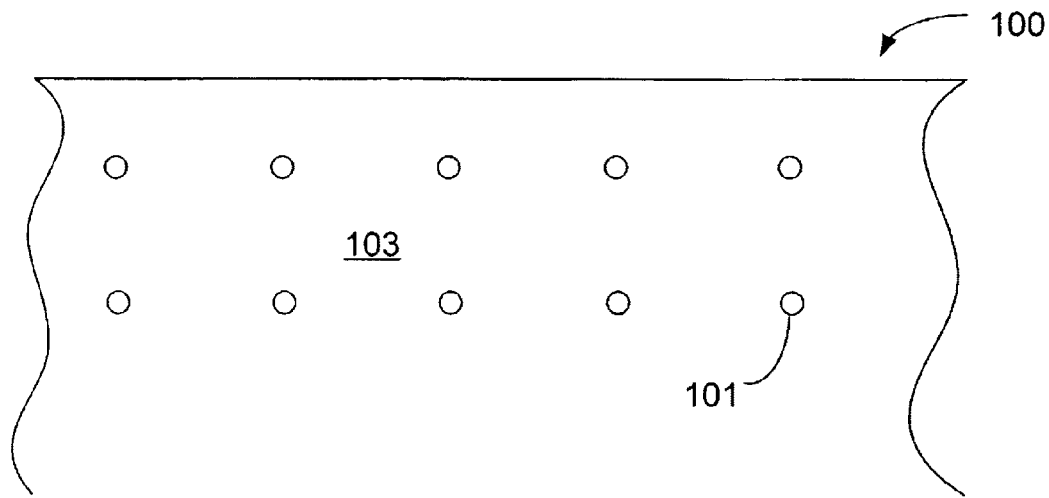
FIGS. 1 through 5 illustrate a method according to an embodiment of the present invention.

FIGS. 1 through 5 illustrate methods according to an embodiment of the present invention. These diagrams are merely an illustration and should not unduly limit the scope of the claims herein. One of ordinary skill in the art would recognize many other variations, modifications, and alternatives. As shown in FIG. 1, the method begins by providing a silicon wafer 100. The silicon wafer is a P-type wafer having an impurity resistivity of boron of about 2–5 ohms/cm, but can be others. As shown, the silicon atoms are arranged in a crystalline structure 101, 103 of crystal orientation or others. The silicon wafer is a test wafer to be placed into an implantation tool to be monitored before release into production.

Figure 2:
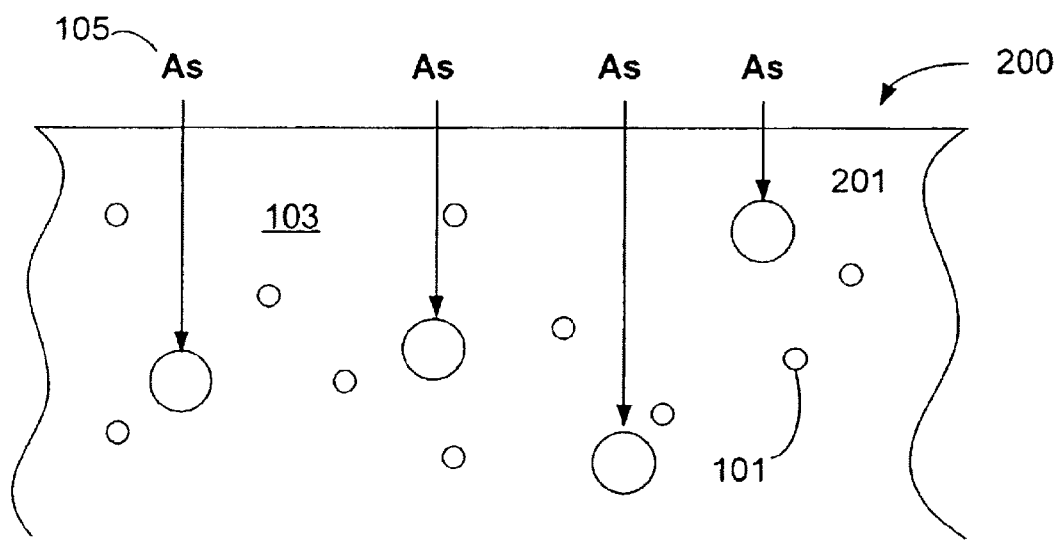

Referring to FIG. 2, arsenic bearing impurities 105 are introduced through a surface of the wafer to a selected depth 201. The arsenic bearing impurities are often introduced at a dose ranging from about $1.0\ E^{12}$ to about $1.0\ E^{13}$. Depending upon the application, other impurities can also be used. Such impurities are often ones that do not substantially migrate upon subsequent thermal treatments. The arsenic bearing impurities increase a conductivity of the silicon material and serves as a base implant.

Figure 3:
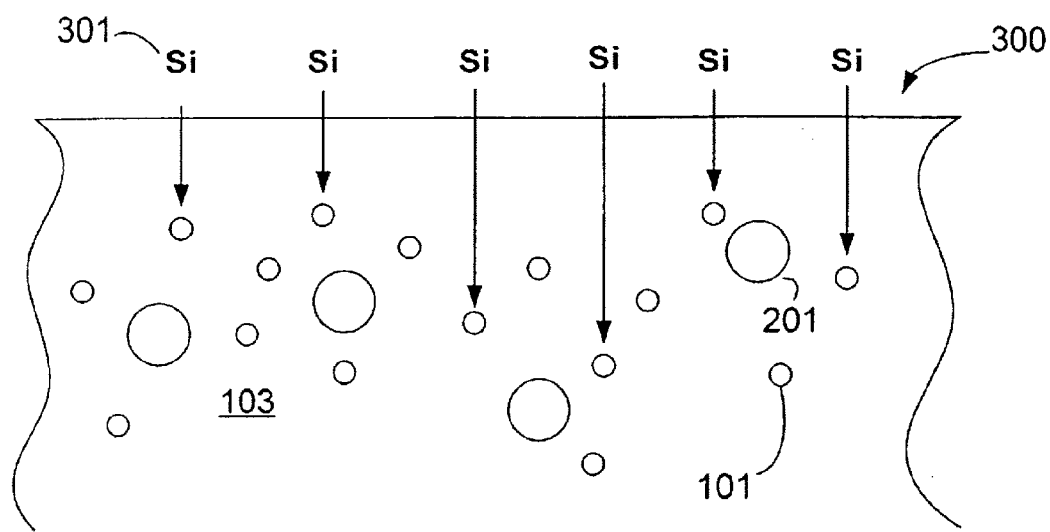
Figure 4:
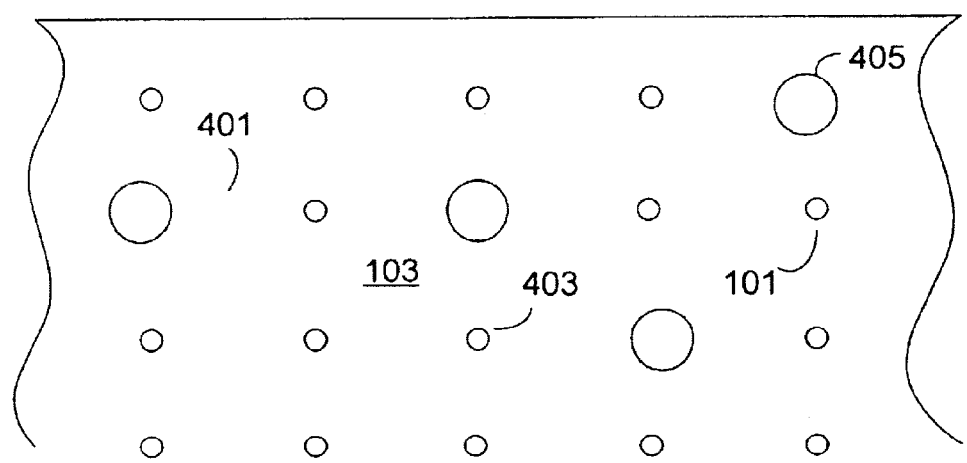
Figure 5:
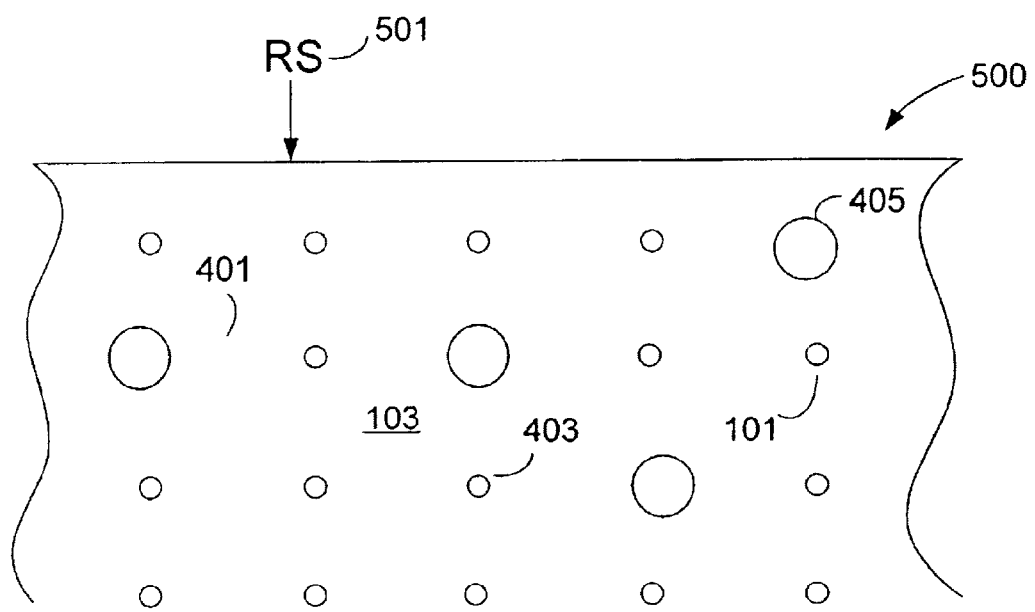

The method then introduces silicon bearing impurities 301 through the surface of the substrate as shown in FIG. 3. The silicon bearing impurities are often derived from silane gas, such as $SiF_4$. Depending upon the application, there can be other ways of deriving silicon bearing impurities. The implanted substrate is subjected to an anneal process, as illustrated by FIG. 4. The anneal process causes the silicon ions to migrate into the lattice structure 403 as shown. Additionally, arsenic bearing impurities are also activated into the substrate. Preferably, a rapid thermal process is used. Such rapid thermal process subjects the implanted substrate to a temperature ranging from about 950° to about 1050° in an inert environment. Here, the environment can include nitrogen gas or other suitable non-reactive gas in certain embodiments. The method then measures a sheet resistance value of the substrate 500, as shown by FIG. 5. The sheet resistance value is often measured by RS-75 tool, but can be others. Preferably, the sheet resistance increase for higher doses of silicon bearing impurities. Here, the high resistance is caused by a lower density of arsenic bearing impurities, which dope the silicon substrate. Further details of this invention can be found throughout the present specification and more particularly according to the example below.

It is also understood that the examples and embodiments described herein are for illustrative purposes only and that various modifications or changes in light thereof will be suggested to persons skilled in the art and are to be included within the spirit and purview of this application and scope of the appended claims.

EXAMPLE

To prove the principle and operation of the present invention, we performed experiments. This example is merely an illustration and should not unduly limit the scope of the claims herein. One of ordinary skill in the art would recognize many other variations, modifications, and alternatives. In these experiments, we used two test wafers. Each of the test wafers was P-impurity type wafer. Such wafers had a concentration of about 2~5 ohms/cm boron bearing impurities. These wafers were each implanted using the values and measurements provided in Table 1.

TABLE 1

| | Wafer Run Data | | | |
|---|---|---|---|---|
| Wafer Number | Dose (%) | TW | TW (change %) | TW (sensitivity) |
| 1 | 100 | 930.1 | N/A | N/A |
| 2 | 105 | 938.2 | 0.87 | 0.174 |

As shown, silicon was implanted at 35 KeV at 8E14 atoms/cm2. A thermal wave value was measured using a Thermal Wave TP 500. The first wafer was at a 100% dose and the second wafer was at a 105% dose, which yielded TW values of respectively 930.1 and 938.2. The TW change % was less than 1%, i.e., 0.87%. The % change has been calculated as follows:

TW (change %)=[(938.2−930.1)/930.1]*100=0.87%

The TW sensitivity was 0.174. As shown below, the sensitivity has been calculated as follows:

TW sensitivity=(0.87%/5%)=0.174 where:
0.87% is the percentage change in TW; and
5% is the percentage change in doses from wafer 1 to wafer 2.

Such sensitivity is not very accurate and can lead to difficulties in monitoring small changes in implant dosage values, which is a limitation of the conventional method.

We next ran wafers using aspects of the present method. Referring to Table 2, two wafers were prepared.

TABLE 2

Wafer Run Data

| Wafer Number | Dose (%) | Rs | Rs (change %) | Rs (sensitivity) |
|---|---|---|---|---|
| 1 | 100 | 2244 | N/A | N/A |
| 2 | 105 | 2351 | 4.77 | 0.954 |

The first wafer was at a 100% dose and the second wafer was at a 105% dose, which yielded sheet resistance values of respectively 2244 and 2351. The change is sheet resistance was 4.77%. A sheet resistance sensitivity value was calculated to be almost 1, which tracks the change in dosage. The method implanted silicon atoms at 30 KeV using a dose of 5.0E15 on pre-treated wafers, which were annealed after implantation. The pre-treated wafers were made by implanting arsenic bearing impurities at 60 KeV at a dose of 5.0E12 on P-type impurity test wafers. As shown, the Rs change was much more sensitive to small changes in implantation doses, which allows us to monitor implantation processes much more efficiently than conventional processes.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for monitoring a dose of a silicon-bearing implant, the method comprising:
   introducing a first implant species through a surface of a semiconductor substrate at a first dose and a first energy level;
   introducing a silicon bearing species through the surface of the semiconductor substrate at a second dose and a second energy level;
   annealing the semiconductor substrate;
   measuring a sheet resistance value of the surface of the semiconductor substrate; and
   determining the second dose value based upon the surface resistance value.

2. The method of claim 1 wherein the first implant species is an arsenic-bearing species.

3. The method of claim 1 wherein the first dose is less than the second dose.

4. The method of claim 3 wherein the first dose is at least three orders of magnitude less than the second dose.

5. The method of claim 1 wherein the sheet resistance value is an Rs value.

6. The method of claim 1 wherein the first implant species is selected from arsenic or indium or antimony.

7. The method of claim 1 further comprising repeating the steps of introducing the silicon-bearing species for other doses and other energy levels.

8. The method of claim 1 wherein the annealing is provided using a rapid thermal anneal and maintained in a non-reactive environment.

9. The method of claim 1 wherein the semiconductor substrate is a P-type silicon substrate.

10. The method of claim 1 wherein the annealing activates the first implant species.

11. The method of claim 1 wherein the annealing is provided in a non-reactive environment.

12. The method of claim 11 wherein the non-reactive environment is a nitrogen-bearing gas.

13. A method for manufacturing integrated circuits on semiconductor substrates, the method comprising:
    inserting a test substrate into an implant tool;
    introducing a base implant species through a surface of the test substrate at a base dose and a base energy level;
    introducing a silicon-bearing species through the surface of the test substrate at a first dose and a first energy level;
    annealing the test substrate in an inert environment;
    measuring a sheet resistance value of the surface of the test substrate, the sheet resistance value being based upon at least the first dose of the silicon-bearing species;
    determining the first dose value based upon at least the surface resistance value; and
    using the first dose to calibrate the implantation tool for a manufacture of semiconductor substrates; and
    using the implantation tool for the manufacture of semiconductor substrates.

14. The method of claim 13 wherein the base dose is less than the first dose.

15. The method of claim 13 wherein the first dose is at least three orders of magnitude less than the second dose.

16. The method of claim 13 wherein the sheet resistance value is an Rs value.

17. The method of claim 13 wherein the base implant species is arsenic.

18. The method of claim 13 wherein the semiconductor substrates are production wafers.

19. The method of claim 13 wherein the annealing is provided using a rapid thermal anneal and maintained in a non-reactive environment.

20. The method of claim 13 wherein the semiconductor substrate is a P-type silicon substrate.

* * * * *